CHRYSANTHEMUM PLANT
Filed Jan. 2, 1973 2 Sheets-Sheet 1
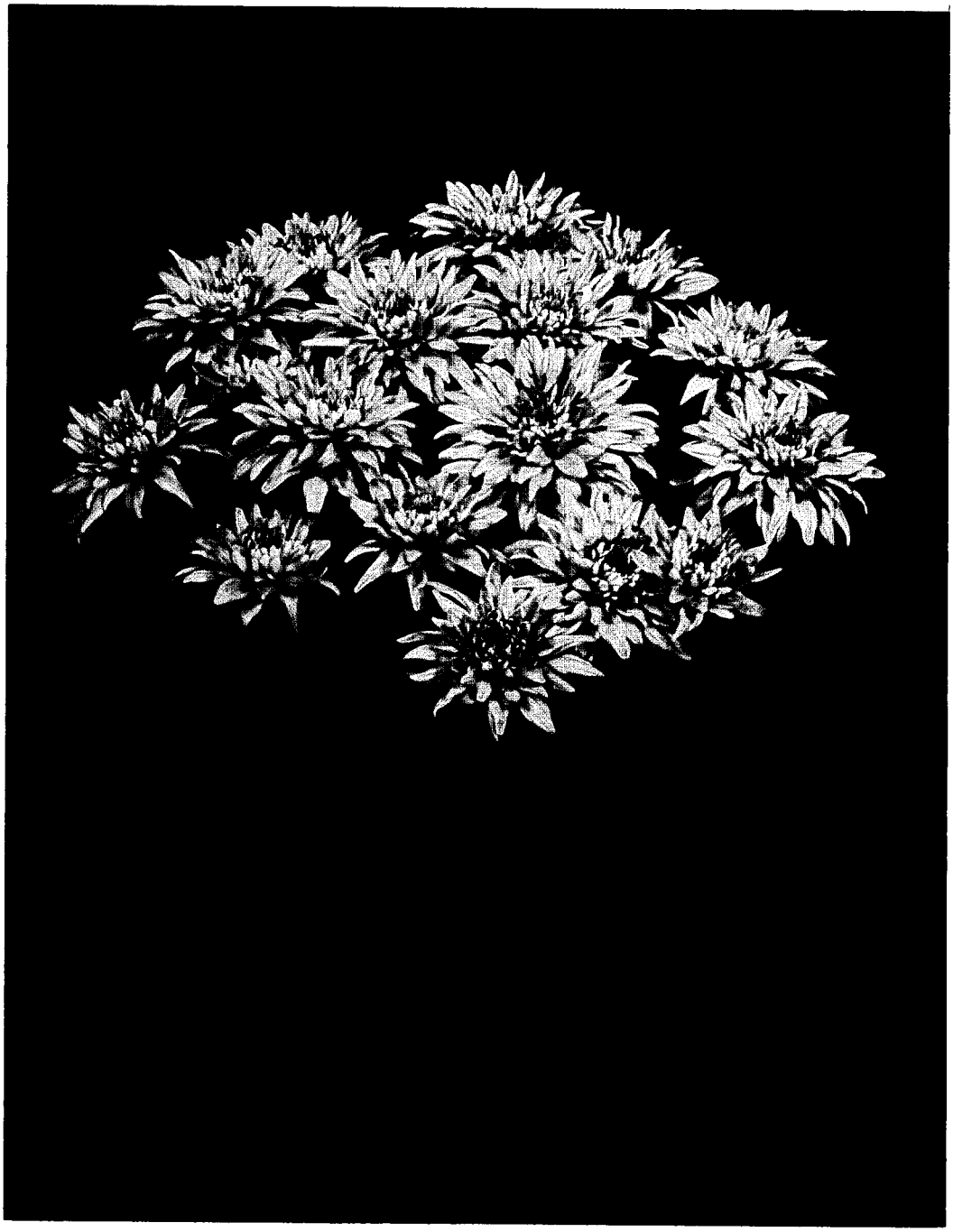

CHRYSANTHEMUM PLANT
Filed Jan. 2. 1973 2 Sheets-Sheet 2
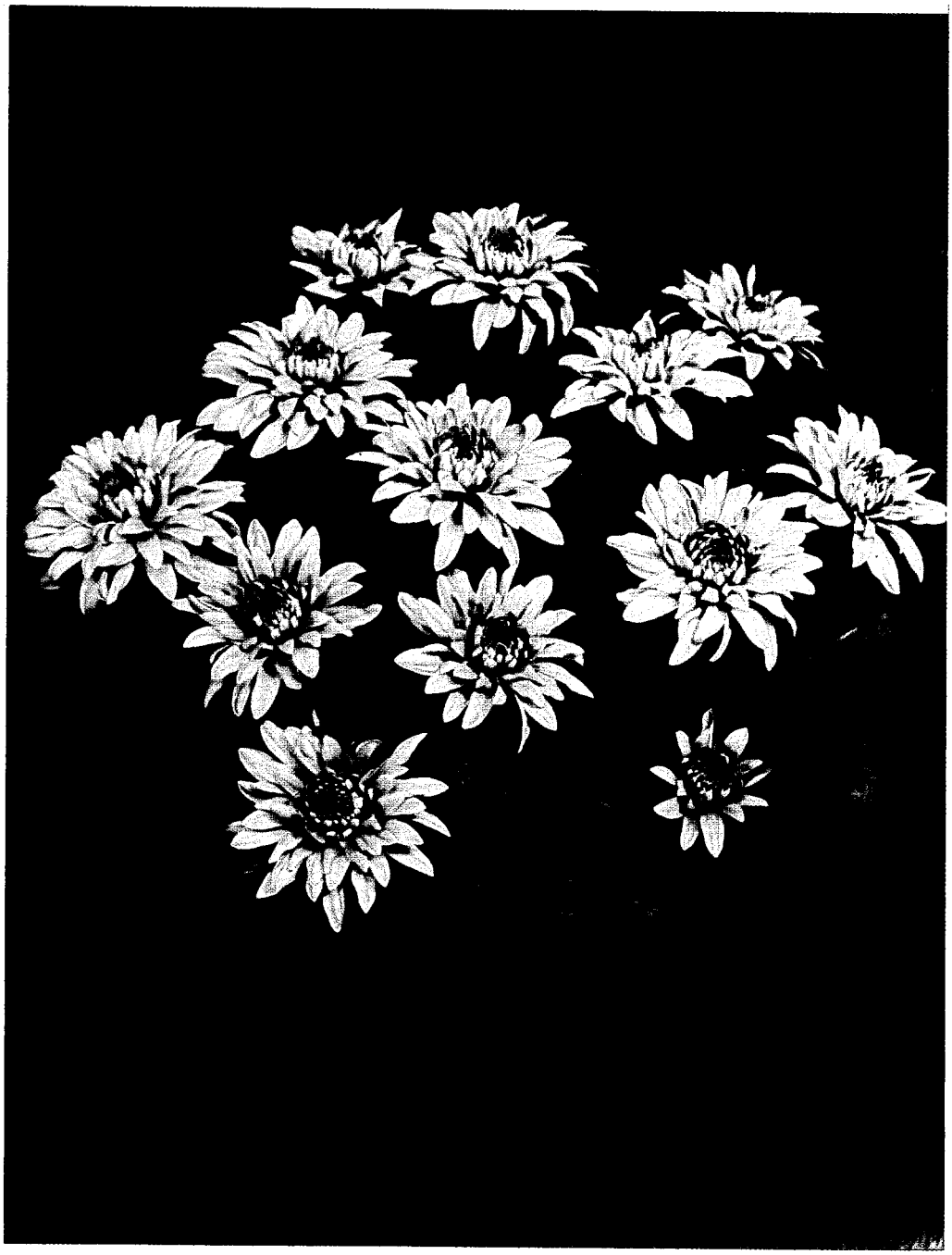

United States Patent Office

Plant Pat. 3,549

Patented May 14, 1974

3,549

CHRYSANTHEMUM PLANT

Edmund R. Niklas, 12059 SE. Valley View Terrace, Clackamas, Oreg. 97015, and Walter H. Jessel, Jr., Doylestown, and William E. Duffett, Akron, Ohio; said Jessel and said Duffett assignors to said Niklas

Filed Jan. 2, 1973, Ser. No. 320,112

Int. Cl. A01h *5/00*

U.S. Cl. Plt.—76 1 Claim

The present invention comprises a new and distinct cultivar of chrysanthemum plant known by the varietal name Royal Trophy, which is a sport of the unpatented cultivar known in the United States as Illini Trophy.

The new cultivar is similar in many respects to Illini Trophy, having the same characteristics of:

1. Year round period of value.
2. Responsiveness to growth regulators, particularly B–9.
3. Recommended short treatment. Like Illini Trophy, medium treatment may be used if B–9 is not applied until late in the development of the crop.
4. Foliage form.
5. Growth habit.

The new cultivar is distinguished from Illini Trophy by the following characteristics when grown under comparable conditions:

1. A more intense deep lavender color.
2. A flower approximately ¼″ smaller in diameter.
3. Approximately 2 to 5 days earlier response, with the response also being more uniform from plant to plant within a multiplant container.
4. A darker green foliage.

5. Foliage smaller in length and width.
6. Approximately 2″ to 3″ shorter growth habit.
7. A flatter decorative flower form which has less tendency than Illini Trophy to develop reflexing of the petals and a higher crowned flower.

The new cultivar was discovered under cultivation in a greenhouse in Clackamas, Oregon, and has been asexually reproduced by cuttings at Barberton, Ohio. The new cultivar has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. It can be flowered year round in all areas of the United States.

The accompanying drawings comprise color photographs of the new cultivar in pot form. Sheet 1 was taken in early October under relatively high light conditions, with the flower color being somewhat lighter and the flower form more open. Sheet 2 comprises a photograph taken in February and shows a somewhat darker flower color and tighter flower form.

In the following description, color references are made to the Munsell Limit Color Cascade Chart, 1972 edition, and comparisons are made with the parent cultivar Illini Trophy to develop reflexing of the petals and a higher for the new cultivar, the same value or description applies as well to the comparison cultivar.

Botanical classification: *Chrysanthemum morifolium*

| | Royal Trophy | Illini Trophy |
|---|---|---|
| Bloom: | | |
| Size | 4¾″ | 5″. |
| Fully expanded | 5¼″ | 5½″. |
| Borne | Singly on disbudded stems | |
| Stems | Strong | |
| Form | Flat decorative | Reflexed decorative. |
| Permanence | 10–12 days | |
| Color: | | |
| Center of flower | Dark lavender, 45–9 over light lavender, 46–2 | Lavender, 46–6. |
| Base of petals | Yellow-green, 22–3 | Yellow-green, 22–3. |
| Inside of petals | Dark lavender, 46–7 over lavender, 45–5 | Lavender 46–6 over light lavender, 45–2. |
| Reverse of petals | Lavender, 45–5 over light lavender, 46–1 | Lavender, 45–3 over light lavender, 45–1. |
| Tonality from a distance | Purple | Lavender. |
| Discoloration | Dark lavender, 46–7 over lavender, 45–5 | Lavender, 46–4 over light lavender, 45–2. |
| Petals: | | |
| Texture | Smooth | |
| Appearance and form | Open at base, flat shallow keel tapering to blunt petal tip with slight reverse roll of petal edges. | |
| Arrangement | Composite, whorled on a single receptacle | |
| Persistence | Resist shatter | |
| Fragrance | Typical chrysanthemum | |
| Reproductive organs: | | |
| Stamen, anthers | 0–5 | |
| Pollen | None to very scant | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Semi-upright | |
| Height | Approximately 11″–12″ when grown in a 5-cutting, 6″ pot, given 9 week short treatment as defined in the pot mum timetable of Yoder Brothers, Inc., Barberton, Ohio, for the various seasons of the year. | Approximately 13″–15″ when grown in a 5-cutting, 6″ pot, given 9 week short treatment as defined in the pot mum timetables of Yoder Brothers, Inc., Barberton, Ohio, for the various seasons of the year. |
| Spread | Approximately 9″ when grown in a 5-cutting, 6″ pot, given 9 week short treatment as defined in the pot mum timetables of Yoder Brothers, Inc., Barberton, Ohio, for the various seasons of the year. | |
| Foliage: | | |
| Top side | Dark green, 17–15 | Green, 18–15. |
| Size | 4½″ long, 3″ wide | 5″ long, 3½″ wide. |
| Quantity | Numerous | |
| Shape | Spatulate lobed | |
| Texture | Coarse | |
| Ribs and veins | Prominent | |
| Edge | Moderately indented | |
| Serration | Coarse | |
| Under side | Medium green, 19–14 | Light green, 20–14. |
| Stipules | Prominent | |

We claim:

1. A new and distinct cultivar of chrysanthemum characterized particularly as to its uniqueness when compared to the parent cultivar Illini Trophy by its more intense deep lavender color; flowers approximately ¼" smaller in diameter; darker green foliage which is smaller in length and width; approximately 2" to 3" shorter growth habit, approximately 2 to 5 days earlier response which is also more uniform from plant to plant, and by its flatter decorative flower form which has less tendency than Illini Trophy to develop reflexing of the petals and a higher crowned flower.

No references cited.

ROBERT E. BAGWIILL, Primary Examiner